United States Patent [19]

Driscoll et al.

[11] Patent Number: 4,986,885
[45] Date of Patent: Jan. 22, 1991

[54] PROCESS FOR THE SEPARATION OF BUTANOL AND BUTOXYACETALDEHYDE

[75] Inventors: Robert K. Driscoll, Frankfurt am Main; Ingo Leupold, Neu-Anspach; Karl-Heinz Schönwälder, Kelkheim, all of Fed. Rep. of Germany

[73] Assignee: Hoechst Aktiengesellschaft, Frankfurt am Main, Fed. Rep. of Germany

[21] Appl. No.: 329,942

[22] Filed: Mar. 29, 1989

[30] Foreign Application Priority Data

Mar. 31, 1988 [DE] Fed. Rep. of Germany ....... 3811059

[51] Int. Cl.$^5$ .......................... B01D 3/10; C07C 45/82
[52] U.S. Cl. ...................................... 203/73; 203/81; 568/492; 568/496
[58] Field of Search ....................... 568/492, 496, 913; 203/73, 91, 81, 14, 18

[56] References Cited

U.S. PATENT DOCUMENTS 3,481,837  12/1969  Johnson et al. ..................... 568/492
3,505,407  4/1970   Cavitt ................................. 568/492
4,233,246  11/1980  Dudeck et al. ..................... 568/496

OTHER PUBLICATIONS

Technique of Organic Chemisty–Distillation 1951, N.Y., p. 463, Weissberger.
Drake et al.; Journ. Am. Chem. Soc., vol. 60, (1938) pp. 73–76.
Keiko et al., Prikl. Zh. Chim. (Leningrad) 43 (1970) 1137–1140.

Primary Examiner—Wilbur Bascomb

[57] ABSTRACT

A process for the separation of butanol and butoxyacetaldehyde which involves subjecting a composition which contains these two compounds to a distillation at a pressure of at most 660 mbar. According to a special embodiment the composition to be distilled contains as essential components water, butanol, butoxyacetaldehyde, butylglycol and, if desired, also butyraldehyde.

12 Claims, No Drawings

PROCESS FOR THE SEPARATION OF BUTANOL AND BUTOXYACETALDEHYDE

DESCRIPTION

The invention relates to a process for the separation of butanol and butoxyacetaldehyde.

Alkoxyacetaldehydes are valuable starting materials for the preparation of dyes, plastics, fragrance materials, resins and elastomers. Their preparation by dehydrogenation or oxydehydrogenation of ethylene glycol monoalkyl ethers (alkyl glycols) has frequently been described in the literature, for example by Drake et al., Journ. Am. Chem. Soc. 60 (1938), 73–76 and Keiko et al., Prikl. Zh. Chim. (Leningrad) 43 (1970), 1137–1140. It is generally known that these compounds undergo selective oxydehydrogenation only with difficulty (Houben-Weyl 7/1 (1954), pages 166 and 167). A preferred side reaction is the elimination of the alkoxy group in the form of the corresponding alcohol.

Drake et al. describe the qualitative isolation of methoxy- and ethoxyacetaldehyde as such or as an azeotrope with water. However, they were unable to isolate a major part of the desired products, which was instead polymerized to high-boiling polymers. It is also mentioned there that the isolation of n-butoxyacetaldehyde is even more difficult. Keiko et al. likewise describe a qualitative separation of alkoxyacetaldehydes, including butoxyacetaldehyde, from reaction mixtures of this type, which inevitably also contain water. However, no information is given about the yields in the isolation of butoxyacetaldehyde.

U.S. Pat. Nos. 3,481,837 and 3,505,407 describe processes for the isolation of methoxyacetaldehyde from the reaction product of the oxidation of methylglycol. It is stated there that complete separation of methanol and methoxyacetaldehyde by distillation is scarcely possible, despite a sufficient difference in boiling points. However, methanol and water could be separated from methoxyacetaldehyde by the addition of a certain entraining agent (acetonitrile or chloroform) and subsequent azeotropic distillation, so that methoxyacetaldehyde was obtained in a yield of 76% and with a purity of more than 95%. The remaining methoxyacetaldehyde was lost as high-boiling polymer. However, the addition of an entraining agent makes it necessary to carry out additional separation stages in order to separate methoxyacetaldehyde from the entraining agent and in order to be able to recycle pure entraining agent to the process.

A detailed process for the isolation of butoxyacetaldehyde has not been described to date.

It has been found, surprisingly, that butanol and butoxyacetaldehyde can readily be separated from one another by distillation in a certain pressure range, in particular under a pressure of not more than 660 mbar. The use of an additional entraining agent is not necessary.

The invention also permits the isolation of butoxyacetaldehyde from mixtures which have a more complex composition and also contain butanol. Thus, with the aid of the process according to the invention, it is possible to isolate the butoxyacetaldehyde from mixtures which also contain water in addition to butanol. This is permitted by virtue of the fact that, as has likewise been found, n-butoxyacetaldehyde forms with water a lower-boiling azeotrope, which separates into two phases after condensation. If the upper, organic phase is recycled to the distillation, the water can be separated off in this manner, resulting in a considerable simplification.

However, it is also possible to separate mixtures having an even more complex composition with the aid of the process according to the invention, for example those which essentially contain water, butoxyacetaldehyde, butanol and butylglycol and may contain further substances, such as butyraldehyde. Mixtures of this type are obtained, for example, in the catalytic oxydehydrogenation of butylgycol, such as n-butylglycol, in the gas phase. To separate such mixtures, it is advantageous, according to the invention, to use a procedure in which (a) in a first stage, the water is distilled over the top as an azeotrope with the butoxyacetaldehyde, the condensed distillate is allowed to separate into two phases and the upper, organic phase is recycled to the distillation, (b) in a second stage, the bottom product (a) is distilled under a pressure of not more than 660 mbar, butanol and the remaining low boilers being removed via the top and essentially a bottom product comprising butoxyacetaldehyde and butylglycol being obtained, and (c) in a third stage, virtually pure butoxyacetaldehyde is distilled off via the top from the bottom product of (b), so that butylglycol remains behind as a bottom product.

The first stage is generally carried out in the range from 10 to 2000 mbar, preferably from 50 to 660 mbar. For example, a column for which only a few theoretical plates are required is suitable. Predominantly water and any butyraldehyde and butanol present are removed, these being known to form azeotropes with water. Since butoxyacetaldehyde likewise forms an azeotrope with water, mixtures of butanol, butyraldehyde, water and considerable amounts of butoxyacetaldehyde are obtained at the top during the distillation. However, in the liquid state the three stated organic substances have limited mixability with water, so that the distillate separates into two phases. Thus, the lower phase contains about 90% by weight of water at 20° C., while the upper, organic phase contains about 11% by weight of water. About 90% of the butoxyacetaldehyde present in the distillate appear in the upper phase. This is recycled to the distillation, i.e. it is used to remove the water by entrainment.

Very little (about 2%) of the butoxyacetaldehyde present in the starting mixture is lost in the aqueous phase. If desired, these small losses can be avoided by extracting the aqueous phase with conventional extracting agents, for example butyraldehyde or butanol. Thereafter, the butoxyacetaldehyde must be separated from the extracting agent by distillation, which would normally entail a great deal of effort for a small amount of product.

The starting material for the second stage contains essentially butanol, butoxyacetaldehyde, butylglycol and butyraldehyde. In this stage, butanol is substantially separated from butoxyacetaldehyde. For this purpose, it is necessary to maintain a pressure of not more than 660 mbar. In general, the pressure is not less than 16 mbar.

The complicated distillation behavior of mixtures of butanol and butoxyacetaldehyde is evident from the fact that, for example, first pure butoxyacetaldehyde and then a mixture of butanol and butoxyacetaldehyde are distilled off under 16 mbar from such mixtures, which contain only a relatively small proportion of n-butanol. The bottom product obtained after the distillation still contains a large amount of butanol. Thus, under 16 mbar, butanol and butoxyacetaldehyde can be separated from one another partially but not completely. If the same mixture is distilled under 395 mbar, first pure n-butanol and then butoxyacetaldehyde are obtained, as would be expected from the boiling points (b.p. 94° C. and 117° C., respectively). The two substances thus pass over in the opposite order to that under 16 mbar. Although separation of butanol and butoxyacetaldehyde by distillation is good under a pressure of 395 mbar, there is a danger that some of the butoxyacetaldehyde will decompose to give high-boiling polymers. This decomposition which takes place under relatively high distillation pressures can, however, be reduced by using a continuous procedure, since in this case the residence time of the butoxyacetaldehyde in the bottom of the column is shorter.

For the reasons stated above, the distillation is advantageously carried out in the range from 16 to 395 mbar, preferably from 40 to 260 mbar and in particular from 65 to 200 mbar.

In the separation of the abovementioned mixtures having a complicated composition, the starting material for the third stage consists essentially of butoxyacetaldehyde and butylglycol. In this stage, virtually pure butoxyacetaldehyde is obtained at the top, while butylglycol is obtained as a bottom product. The butylglycol can be reused in the oxidation reactor. This distillation is generally carried out in the range from 2 to 1000 mbar, preferably from 10 to 250 mbar. However, 10 to 160 mbar are particularly preferred.

The three stages can be carried out both batchwise and continuously, for example using distillation columns. A continuous procedure is preferred, at least for stages (b) and (c). Such a procedure is particularly advisable when distillation is carried out under relatively high pressures.

If the first stage is carried out batchwise, the organic phase can be recycled to the top until an aqueous phase no longer forms; the low-boiling butyraldehyde can then be distilled off. If, on the other hand, the first stage is carried out by a continuous procedure, it is advisable to wait until the second stage before removing the butyraldehyde and any residual water still present, together with butanol, via the top.

In another embodiment, it is possible to separate mixtures which contain butanol, butoxyacetaldehyde and butylglycol and may contain further substances, such as water and butyraldehyde, by a procedure in which first the lower boiling substances are separated by distillation from the butylglycol, which has the highest boiling point and therefore remains behind as a bottom product, and the distillate is then worked up by the procedure stated for stages (a) and (b). However, this embodiment is less preferred.

Any butyraldehyde present is discharged regularly with the butanol.

The butyl groups in butylglycol, butanol and butoxyacetaldehyde can be primary, i.e. normal or iso-, secondary or tertiary. However, they are all preferably n-butyl groups.

Below, the percentages are based on weight. The starting material used in the examples is a crude product which was prepared with the aid of a silver catalyst on an aluminum silicate carrier, as follows:

200 g/h of n-butylglycol were metered into an evaporator at 300° C., together with 3980 l(s.t.p.)/h of $N_2$ and 320 l(s.t.p.)/h of air. This mixture was then brought to 420° C. in a preheater and was fed to the reactor. The maximum reaction temperature was measured with a mobile thermocouple, and was 420° C. The residence time in the reactor was about 0.27 second. At the reactor outlet, the gaseous reaction product was cooled, first with a water cooler and then with a brine cooler (T = −10° C.). 201.2 g/h of condensate having the following composition were obtained 77.2% of n-butoxyacetaldehyde, 5.0% of n-butylglycol, 3.1% of n-butanol, 1.0% of n-butyraldehyde and 11.7% of water. CO, $CO_2$ and a little water and butanol were not condensed. The yield was 79% at 95% conversion.

EXAMPLES (1) 1st stage—3 kg of the condensate mixture were heated under 100 mbar in a 6 l flask connected to a water separator. The temperature at the top increased rapidly to 45° C., which approximately corresponds to the boiling point of water under this pressure. However, the distillate contained only about 50% of water and also n-butoxyacetaldehyde, n-butyraldehyde, n-butanol and a little n-butylglycol, i.e. the distillate was an azeotrope containing a plurality of components. After the condensation, the distillate separated into an upper, organic phase, which contained a small amount of water, and a lower phase, which consisted of about 89% of water. The upper phase was recycled to the flask continuously during the distillation. The distillation was continued until the condensed distillate consisted of only one phase and the temperature at the top had increased to 60° C. This single-phase distillate was finally added to the bottom product of the distillation.

During the distillation, 384 g of aqueous phase having the following composition were removed: 88.8% of water, 7.8% of n-butoxyacetaldehyde, 1.3% of n-butanol, 0.8% of n-butyraldehyde and 1.3% of other substances. 2602 g of bottom product having the following composition were obtained: 87.9% of n-butoxyacetaldehyde, 5.8% of n-butylglycol, 3.4% of n-butanol, 0.6% of n-butyraldehyde, 0.3% of water and 2.1% of other substances. Thus, more than 97% of the water were removed from the starting material, only about 1.3% of the n-butoxyacetaldehyde present therein being lost with the aqueous phase.

2nd stage—100 g/h of the bottom product obtained above were preheated to 83° C. and fed into the lower third of a silver-jacketed distillation column which had a diameter of 2.5 cm and contained a 120 cm high layer of Braunschweig glass coils. The distillation was carried out under 132 mbar; the reflux ratio was 14:1. A fraction having a boiling point of 70° C. and containing n-butanol and other low boilers was obtained at the top. 95.9 g/h of a product composed of 90.2% of n-butoxyacetaldehyde, 5.9% of n-butylglycol, 0.4% of n-butanol and 3.4% of other substances were removed from the bottom.

3rd stage—The product bottom obtained in the second stage was fed, at 78° C., into the upper third of a second distillation column. This column, likewise with a silver jacket, had the same diameter and also contained a 120 cm high layer of Braunschweig glass coils. The distillation was carried out under 66 mbar; the reflux ratio was 3:1. 85.2 g/h of distillate which had a boiling point of 71° C. and consisted of 99.5% of n-butoxyacetaldehyde and 0.5% of n-butanol at the top were obtained. A mixture of n-butylglycol and other high boilers was obtained as a bottom product.

In this example, more than 95% of the n-butoxyacetaldehyde present in the oxidation product could be obtained with a purity of 99.5%.

Freshly distilled n-butoxyacetaldehyde has a luminous greenish color. After a few hours, the liquid loses its color and the aldehyde is predominantly in the form of oligomers. The monomeric aldehyde can readily be recovered from this, for example by simple distillation under reduced pressure.

(2) 500 g of the bottom product obtained from the first stage of Example 1 were distilled batchwise in a silver-jacketed column (length 120 cm, diameter 2.5 cm, packing: Braunschweig glass coils, reflux ratio 6:1) under 132 mbar. After the remaining n-butyraldehyde and water had been removed, the temperature at the top increased to 70° C., corresponding to the boiling point of n-butanol under this pressure. The distillation was continued until the temperature at the top increased substantially. At the end, 479 g of a product having the following composition were obtained at the bottom: 89.0% of n-butoxyacetaldehyde, 5.9% of n-butylglycol, 0.4% of n-butanol and 4.6% of other substances. About 90% of the n-butanol present in the starting material had been removed via the top; 97% of the n-butoxyaldehyde were recovered. This product was further processed as described in the third stage in Example 1.

(3) Example 2 was repeated using a further 500 g of the bottom product obtained in the first stage of Example 1. However, the distillation was carried out under 395 mbar. After the remaining n-butyraldehyde and water had been removed, the temperature at the top increased to 94° C., corresponding to the boiling point of n-butanol under this pressure. At the end of the experiment, the bottom contained 477 g of a mixture having the following composition: 69.1% of n-butoxyacetaldehyde, 4.9% of n-butylglycol, 0.4% of n-butanol and 25.6% of other substances. Here, about 90% of the n-butanol present in the starting material were likewise removed. However, about 25% of the n-butoxyacetaldehyde had decomposed, a high-boiling product being formed in the bottom.

(4) Example 2 was repeated using a further 500 g of the bottom product obtained in the first stage of Example 1. Here, however, the distillation was carried out under 16 mbar. The course of the distillation is shown in the table below:

|  | Starting material | Fract. 1 | Fract. 2 | Fract. 3 | Bottom product |
|---|---|---|---|---|---|
| n-Butoxy acetaldehyde | 439.5 | 238.2 | 67.3 | 48.9 | 71.9 |
| n-Butanol | 17 | 2.4 | 2.4 | 3.2 | 8.9 |
| n-Butylglycol | 29 | — | — | — | 28.3 |

After the remaining n-butyraldehyde and water had been removed, the temperature at the top immediately increased to 44° C., approximately corresponding to the boiling point of n-butoxyacetaldehyde. Pure n-butanol boils at 33° C. First, a fraction of virtually pure n-butoxyacetaldehyde was obtained at the top. Further fractions contained increasing amounts of n-butanol, but the temperature at the top remained virtually constant. The bottom product likewise contained a large amount of n-butanol. n-Butanol and n-butoxyacetaldehyde can thus be separated from one another partially, but not quantitatively, by simple distillation under 16 mbar. About 97% of the n-butoxyacetaldehyde were recovered.

We claim:

1. A process for the separation of a composition comprising, butoxyacetaldehyde, butylglycol, water and a compound selected from the group consisting of butanol and mixtures thereof with butyraldehyde, which comprises
   (a) distilling in a first stage the water overhead as an azeotrope with butoxyacetaldehyde, allowing the condensate to separate into two phases and recycling the upper, organic phase into the first distillation stage and obtaining a sump product,
   (b) distilling in a second stage the sump product of stage (a) at a pressure of at most 660 mbar, thus removing overhead butanol and low boiling compounds and obtaining substantially a sump product of butoxyacetaldehyde and butylglycol, and
   (c) distilling in a third stage nearly pure butoxyacetaldehyde overhead from the sump produce of stage (b), thus leaving butylglycol in the sump.

2. A process as claimed in claim 1 wherein the distillation is carried out at a pressure of at least 16 mbar.

3. A process as claimed in claim 1, wherein the distillation in the first stage (a) is carried out in a range of from 10 to 2000 mbar.

4. A process as claimed in claim 3, wherein the distillation in the first stage (a) is carried out in the range of from 50 to 660 mbar.

5. A process as claimed in claim 1, wherein the distillation in the second stage (b) is carried out at a pressure in the range of from 16 to 395 mbar.

6. A process as claimed in claim 5, wherein the distillation in the second stage (b) is carried out a pressure in the range of from 40 to 260 mbar.

7. A process as claimed in claim 6, wherein the distillation in the second stage (b) is carried out at a pressure in the range of from 65 to 200 mbar.

8. A process as claimed in claim 1, wherein the distillation in the third stage (c) is carried out at a pressure in the range of from 2 to 1000 mbar.

9. A process as claimed in claim 8, wherein the distillation in the third stage (c) is carried out at a pressure in the range of from 10 to 260 mbar.

10. A process as claimed in claim 9, wherein the distillation in the third stage (c) is carried out at a pressure in the range of from 10 to 160 mbar.

11. A process as claimed in claim 1, wherein the distillation is carried out in the first stage (a) at a pressure in the range of from 10 to 2000 mbar, in the second stage (b) at a pressure in the range 16 to 395 mbar and in the third stage (c) at a pressure in the range of from 2 to 1000 mbar.

12. A process as claimed in claim 1, wherein the distillation is carried out in the first stage (a) at a pressure in the range of from 50 to 660 mbar, in the second stage (b) at a pressure in the range of from 65 to 200 mbar and in the third stage (c) at a pressure in the range of from 10 to 160 mbar.

* * * * *